United States Patent [19]

Larter

[11] Patent Number: 4,485,071
[45] Date of Patent: Nov. 27, 1984

[54] FIELD SOURCE ROCK EVALUATION APPARATUS

[75] Inventor: Stephen R. Larter, Lake Elsinore, Calif.

[73] Assignee: Union Oil Company of California, Los Angeles, Calif.

[21] Appl. No.: 494,725

[22] Filed: May 16, 1983

[51] Int. Cl.³ .................... G01N 31/12; G01N 33/24
[52] U.S. Cl. ........................ 422/78; 436/31; 436/157; 436/158
[58] Field of Search .............. 422/78, 80; 436/29, 436/31, 32, 157, 158

[56] References Cited

U.S. PATENT DOCUMENTS

| | | | |
|---|---|---|---|
| 2,320,681 | 6/1943 | Thompson | 436/31 X |
| 2,379,045 | 6/1945 | Sturgis | 436/32 X |
| 2,451,883 | 10/1948 | Squires | 436/31 X |
| 2,742,575 | 4/1956 | Bray | 436/29 X |
| 2,854,396 | 9/1958 | Hunt et al. | 436/31 X |
| 3,508,877 | 4/1970 | Heacock et al. | 436/31 X |
| 3,847,549 | 11/1974 | Schorno | 436/31 |
| 4,149,804 | 4/1979 | Chew | 436/31 X |
| 4,149,805 | 4/1979 | Chew | 436/31 X |
| 4,153,415 | 5/1979 | Espitalie et al. | 436/31 X |
| 4,229,181 | 10/1980 | Espitalie et al. | 436/31 X |
| 4,352,673 | 10/1982 | Espitalie et al. | 422/80 X |

Primary Examiner—Arnold Turk
Assistant Examiner—Robert J. Hill, Jr.
Attorney, Agent, or Firm—Robert J. Baran; Gregory F. Wirzbicki; Dean Sanford

[57] ABSTRACT

The hydrocarbon potential of a source rock comprising hydrocarbons and insoluble organic materials capable of generating hydrocarbons upon pyrolysis or further maturation is analytically determined. In the instant invention, a particular sample of the source rock is slurried with a solvent to extract the hydrocarbons therefrom and provide a first solution for analysis. The extracted sample is again slurried with a solvent and the resulting slurry is heated to a temperature sufficient to pyrolyze the insoluble organic material to liquid hydrocarbons. The liquid hydrocarbons dissolve in the solvent to provide a second solution for analysis. The first and second solutions are then analyzed independently for hydrocarbon content.

2 Claims, 1 Drawing Figure

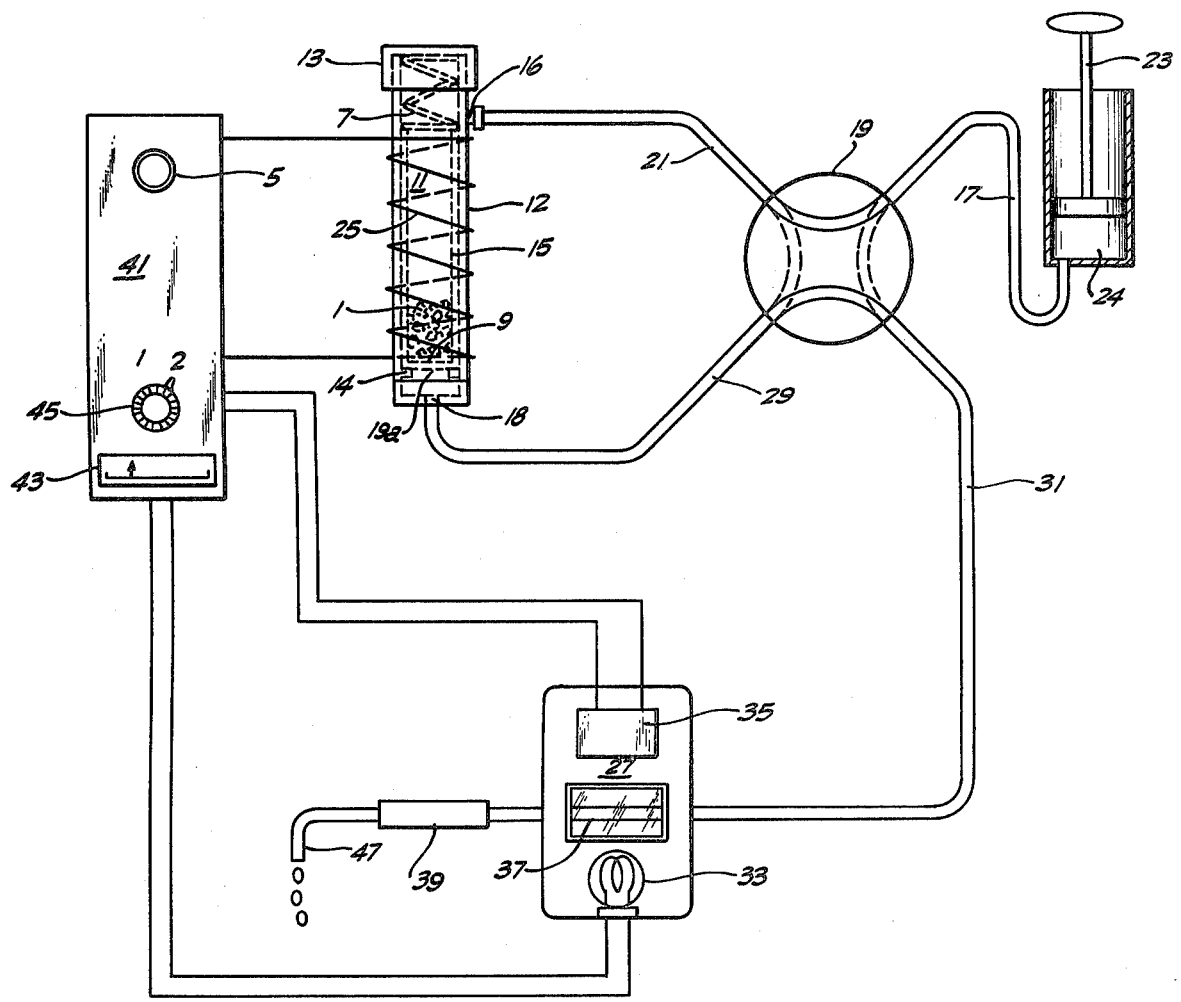

FIELD SOURCE ROCK EVALUATION APPARATUS

BACKGROUND OF THE INVENTION

1. Field of the Invention

This invention relates to a method and apparatus for measuring the hydrocarbon potential of a source rock comprising hydrocarbons and insoluble organic materials capable of generating hydrocarbons upon pyrolysis or further maturation. The apparatus is useful for field evaluation of small samples of suspected oil and gas source rock.

2. Description of the Art

Various geochemical methods have been suggested previously for determining the location and characterization of underground sources of hydrocarbons. These methods detect the presence of hydrocarbons and hydrocarbon precursors in surface or underground formations to determine the potential of such formations for the production of hydrocarbons.

In U.S. Pat. 3,508,877 and 2,451,883 a source rock comprising hydrocarbons and other organic materials which are hydrocarbon precursors is analyzed by the fluorescensc of a sample prepared either by extracting the rock with a solvent or by condensing a vapor removed from the rock by heating. Neither of these methods distinguishes between hydrocarbons present in the source rock as such and organic material which can be converted in hydrocarbons upon pyrolysis or further maturation in situ.

In U.S. Pat. 4,229,181 and 4,153,415 a method and apparatus are disclosed for determining hydrocarbons initially present in a source rock sample and hydrocarbons that may be generated upon pyrolysis thereof. The method and apparatus disclosed in these patents rely upon heating the sample in a gaseous stream to selected temperatures to separately remove the hydrocarbons present in the source rock and the hydrocarbons that may be derived upon pyrolysis. The method and apparatus require a gaseous source and therefore are not as compact nor as easy to operate as is desired in the field.

In U.S. Pat. 4,149,804 and 4,149,805 a method and apparatus to determine the oil content of oil shale are disclosed. These references teach non-destructive methods which rely on the reflectance of light from a solid sample of a source rock to determine the presence of oil therein. In view of the concern of the patentees with determining the richness of oil shale, it is not surprising that this method and apparatus do not distinguish between hydrocarbons initially present in the source rock and hydrocarbons which may be generated upon pyrolysis thereof. Thus, there is no suggestion that this method and apparatus are intended to obtain information about a source rock other than an oil shale.

In view of the foregoing, it is one object of this invention to provide a facile method of analyzing a source rock to determine the hydrocarbon potential thereof, which method is capable of providing information as to both the hydrocarbons initially present and the hydrocarbons that may be generated upon pyrolysis or further maturation of the source rock.

Another object of this invention is to provide an apparatus that is useful in the field for analyzing a source rock for hydrocarbon potential and which does not require operational gases.

These and other objects and advantages of the invention will become apparent in view of the following description.

SUMMARY OF THE INVENTION

This invention provides a method for determining the hydrocarbon potential of a source rock comprising hydrocarbons and insoluble organic material capable of generating hydrocarbons upon pyrolysis which comprises the steps of, (a) slurrying a particulate sample of said source rock with a solvent for dissolving the hydrocarbons initially present in said source rock, (b) removing a first solution comprising said hydrocarbons dissolved in said solvent from said particulate sample, (c) slurrying the particulate sample of step (b) with a solvent, (d) heating the slurry of step (c) to a temperature sufficient to pyrolyze the insoluble organic material in said source rock and provide a second solution of hydrocarbons dissolved in said solvent, and (e) analyzing said first and second solutions for hydrocarbons.

An apparatus useful for carrying out the above method includes:

(a) a solvent reservoir for holding a solvent for said hydrocarbons, (b) a receptacle for receiving a particulate sample of said source rock, (c) detecting means operable to measure the hydrocarbon content of a solution comprising said solvent, and (d) means adapted to sequentially prepare a first sample comprising said initially present hydrocarbons and a second sample comprising the hydrocarbons that may be generated by pyrolysis of said source rock comprising, (1) valve-conduit means, including a valve rotatable between a first and second position, said valve-conduit means being operable to establish sequential fluid communication between said reservoir, said receptacle and said detecting means when said valve is rotated to said first position and said valve being operable to fluid-tightly isolate said receptacle from said reservoir and said detecting means when said valve is rotated to said second position, (2) syringe means operably associated with said reservoir to pass solvent from said reservoir to said receptacle when said valve is rotated to said first position, and (3) heating means operably associated with said receptacle to heat said solvent when said valve is rotated to said second position, said heating means including first temperature regulating means to heat said solvent to a first temperature sufficient to dissolve, but insufficient to pyrolyze said insoluble organic matter, and second temperature regulating means to heat said solvent to a second temperature sufficient to pyrolyze said insoluble organic material.

BRIEF DESCRIPTION OF THE DRAWING FIGURE

The FIGURE schematically illustrates a preferred apparatus for carrying out the method of the instant invention.

DETAILED DESCRIPTION OF THE INVENTION

The instant invention may be understood by reference to a method for using the apparatus disclosed in the FIGURE.

In the apparatus illustrated in the FIGURE, a sample of source rock 1 suspected of having hydrocarbon potential is placed, after grinding to a suitable particle size, in a receptacle 11. As shown, the receptacle comprises a hollow cylindrical housing 12 fitted with a liquid solvent inlet 16 and a liquid solvent outlet 18. Furthermore, housing 12 is provided with an internal axial ridge 14 for supporting an insert 15 that is utilized to hold the sample. The insert 15 is sized to snugly fit within housing 12 and is provided with an apertured bottom 9 having apertures 19a that are sized to permit the passage of solvent but retain the particulate source rock. The insert is open at its top for receiving the sample of source rock. In place, the opening of the insert is below solvent inlet 16, to thereby enable the solvent to pass into the insert for contacting with the particulate sample. The receptacle is provided with screw cap 13 which provides a fluid tight seal at the top of housing 15. As shown, a spring 7 engages the screw cap 13 and the insert 15 to urge the insert against internal axial ridge 14, whereby the action of spring 7 and the sizing of insert 15 ensures that the solvent will pass through the particulate sample and exit the insert through the apertured bottom.

Receptacle 11 is in fluid communication with reservoir 24 through fluid conduit 17, valve 19, fluid conduit 21 and solvent inlet 16. Reservoir 24 is utilized to hold a solvent for the hydrocarbons present in the sample and the hydrocarbons capable of being generated by pyrolysis of the insoluble organic material upon heating. Reservoir 24 is provided with a piston 23 which is used to force solvent contained in reservoir 24 through conduits 17 and 21 into receptable 11 provided that valve 19 is open. Receptable 11 is also provided with a heater 25 in which the solvent contained in receptacle 11 is heated to a first temperature suitable to dissolve hydrocarbons initially present in the source rock and to a second temperature suitable to convert the insoluble organic material present in the source rock into hydrocarbons. Heater 25 may be energized to heat the solvent to said first and second temperatures by first and second temperature regulating means, not shown.

Receptacle 11 is also in fluid communication with a photoelectric cell 27 (or other device for analyzing the amount of hydrocarbon present in a solvent) through fluid conduits 29, valve 19 and fluid conduit 31. As illustrated, valve 19 is open to enable fluid communication between the reservoir, receptacle, and the photoelectric cell. Valve 19 is a two-way valve which can also be rotated from the open first position to a second position to fluid-tightly isolate receptacle 11 from reservoir 24 and photoelectric cell 27.

Photoelectric cell 27 is provided with a light source 33 and detector 35. A portion 37 of fluid conduit 31 is transparent to the light generated by said light source, whereby the light passing from light 33 to detector 35 may be measured. The instant apparatus may also be provided with a window 39 for visual observation of the hydrocarbon-containing solution.

A control unit illustrated at 41 is utilized to detect the signal from detector 35 and provide a readout 43. Moreover, control unit 41 may be utilized to activate the first and second temperature regulating means by switch 45 which is movable between position 1 and 2 to activate either first temperature regulating or second temperature regulating means, respectively. Control box 41 may also be provided with an on-off switch 5 which is utilized to energize both the photoelectric cell 27 and the heater 25.

Preferably, the photoelectric cell 27 is a twin-beam ultraviolet absorption spectrometer. In the twin-beam ultra-violet absorption spectrometer, a sample, containing hydrocarbon dissolved in a solvent, is compared to a reference containing the solvent, alone. The output signal from the spectrometer will be proportional to the difference between the absorbance of the sample and the reference. For greater accuracy the solvent soluble components of the source rock (other than the hydrocarbons) may be dissolved in the solvent by contacting a sample of source rock from which the initial hydrocarbons, and the hydrocarbons derived by pyrolysis, have been removed to provide the reference. The above ultraviolet absorption spectrometer will preferably monitor the differential absorption of the sample and the reference at 300 to 400 nm.

In operation, the sample, after being ground to a convenient particle size, is loaded into insert 15 and the loaded insert is placed in housing 12. The loaded insert 15 is supported on the internal axial ridge 14 of housing 12 and the screw cap 13 is secured to housing 12 to seal the receptacle 11 and urge the insert to seal against the internal axial ridge 14. Valve 19 is rotated to the first position (as shown) to provide fluid communication between the reservoir and the receptacle. Piston 23 is depressed to force solvent from reservoir 24 into the receptacle in an amount sufficient to fill substantially the entire volume of said receptacle, with excess solvent passing through to the photoelectrical cell. Valve 19 is then rotated to the second position to isolate the solvent-filled receptacle from the reservoir and the photoelectric cell. Next, heater 25 is energized to heat the solvent to a temperature of from 50° C. to 300° C. as controlled by said first temperature regulating means. After reaching this temperature and holding thereat for a time period, e.g., from 1 to 10 minutes, sufficient to effect dissolution of initially soluble hydrocarbons, valve 19 is rotated back to the first position and piston 13 is again depressed to pass fresh solvent into receptacle 11. The fresh solvent displaces the hydrocarbon-containing solvent present in receptacle 11 and such hydrocarbon-containing solvent is thereby passed into photoelectric cell 27 for measuring the amount of hydrocarbon present in the solvent by passing a light from lamp 33 through the hydrocarbon-containing solvent to detector 35. The light impinging on detector 35 is converted into a signal which is read at meter 43.

A second heating cycle is then begun by rotating valve 19 back to the second position. Prior to such rotation, however, piston 23 will preferentially be again depressed to send fresh solvent through receptacle 11 and purge any traces of the hydrocarbon-containing solvent from the photoelectric cell through port 47. After displacing the hydrocarbon-containing solvent from the photoelectric cell with fresh solvent, valve 19 is again rotated to the second position and the second temperature regulating means activated to energize the heater so that the fresh solvent is heated to a temperature of from about 350° C. to 500° C. This second temperature will be selected to pyrolyze the remaining organic material present in the sample to yield hydrocarbons. It has been found especially advantageous to utilize a hydrogen donor solvent such as tetralin during this second heating cycle to enable the extraction of hydrocarbon from the insoluble organic material at a lower temperature than in the absence of a hydrogen donor solvent and with less fouling of the receptacle. A hydrogen donor solvent may also be conveniently utilized in the first extraction to dissolve the hydrocarbons initially present in the sample. After reaching the temperature of pyrolysis and holding thereat for a time sufficient to dissolve all of the hydrocarbons derived by pyrolysis of the organic material, e.g. 1 to 10 minutes, or more, valve 19 is again rotated to the first position and a solution containing hydrocarbons dissolved in the hydrogen donor solvent is displaced from receptacle 11 for measurement as before. This second measurement will indicate the amount of hydrocarbons that may be derived upon pyrolysis or further maturation of the source rock. A hydrogen donor solvent also allows the assessment of solubilization of hydrogen deficient materials such as very matured sources, i.e. kerogen or coal.

The following example illustrates a specific method for determining the hydrocarbon potential of a source rock by use of the apparatus described above. This example however, is not to be construed as limiting the scope of the invention which is defined by the appending claims.

EXAMPLE

Approximately ½ gm of oil shale derived from the Colorado River formation is crushed by means of a mortar and pestle and placed in insert 15. The loaded insert is placed in housing 12 and the receptacle 11 is sealed by screw cap 13. Valve 19 is opened and syringe 23 is depressed to pass a pre-measured volume e.g. about 5 cc., of a hydrogen-donor solvent, e.g. tetralin, to fill the receptacle and fill conduits 29 and 31 through to the photoelectric cell 27. Valve 19 is rotated to close and the tetralin in receptacle 11 is heated to 110° C. and held at that temperature for 5 minutes whereby the hydrocarbons, initially present in the shale, are dissolved. Valve 19 is rotated to open and syringe 23 is again depressed to fill the receptacle with fresh tetralin. This filling action passes the heated tetralin, containing the dissolved hydrocarbons, from receptacle 11 to photoelectric cell 27, for measurement of the absorbance of said solution at 300 to 400 nm.

Valve 19 is again rotated to close and the fresh tetralin, in receptacle 11, is heated to 420° C. and held at that temperature for 5 minutes. The insoluble organic material in the shale is thereby converted into tetralinsoluble hydrocarbons, which are dissolved in the tetralin, and passed to photoelectric cell 27 for measurement as described above. While particular embodiments of the invention have been described, it will be understood, of course, that the invention is not limited thereto since many obvious modifications can be made. For example, while the method practiced in the device illustrated in the drawing was manually carried out, control means can be provided to carry out the above method without the operator manually selecting the heating cycle and the valve setting. Moreover, the piston can be replaced with a constant volume delivery pump to automatically pass the solvent into the receptacle without manual intervention by the operator. Thus, the apparatus shown in the FIGURE can further comprise electrical circuit means (e.g. an automatic timer and solenoid system) interconnected with said syringe means, said heating means and said valve means, said circuit means being operative to sequentially:

(i) pass a first portion of solvent from the solvent reservoir to the receptacle, (ii) heat the first portion of solvent to the first temperature, (iii) pass heated first portion of said solvent to the photoelectric cell for measuring the hydrocarbon content thereof, (iv) pass a second portion of solvent to the receptacle, (v) heat the second portion of solvent to the second temperature, and (vi) pass the heated second portion of solvent to the photoelectric cell for measuring the hydrocarbon content thereof.

Moreover, it will be apparent to those skilled in the art that the term hydrocarbons, as used throughout this specification, refers not only to organic materials composed only of hydrogen and carbon, but also to heteroatom-substituted hydrocarbons, e.g., nitrogen, oxygen, and sulfur derivatives of hydrocarbons, found in petroleum, shale, coal, etc. sources of hydrocarbons.

It is intended to include within this invention any obvious modifications as will fall within the scope of the appended claims.

Having now described the invention, I claim:

1. An apparatus for determining the hydrocarbon potential of a source rock comprising hydrocarbons and insoluble organic material capable of generating hydrocarbons upon pyrolysis which comprises:

(a) a solvent reservoir for holding a solvent for hydrocarbons, (b) a receptacle for receiving a particulate sample of a source rock, (c) detecting means operable to measure the hydrocarbon content of a solution comprising said solvent; and (d) means adapted to sequentially prepare a first sample comprising the hydrocarbons initially present in said source rock and a second sample comprising the hydrocarbons that may be generated by pyrolysis of said source rock comprising, (1) valve-conduit means, including a valve rotatable between a first and second position, said valve-conduit means being operable to establish sequential fluid communication between said reservoir, said receptacle and said detecting means when said valve is rotated to said first position and said valve being operable to fluid-tightly isolate said receptacle from said reservoir and said detecting means when said valve is rotated to said second position, (2) syringe means operably associated with said reservoir to transport solvent from said reservoir to said receptacle when said valve is rotated to said first position, and (3) heating means operably associated with said receptacle to heat said solvent, when said valve is rotated to said second position, said heating means including first temperature regulating means to heat said solvent to a first temperature sufficient to dissolve said initially present hydrocarbons, but insufficient to pyrolyze said insoluble organic matter, and second temperature regulating means to heat said solvent to a second temperature sufficient to pyrolyze said insoluble organic material.

2. The apparatus of claim 1 further comprising electrical circuit means interconnected with said syringe means, said heating means, and said valve-conduit means, said circuit means being operative to sequentially:

(i) pass a first portion of solvent from said solvent reservoir to said receptacle, (ii) heat said first portion of solvent to said first temperature, (iii) pass heated first portion of said solvent to said detecting means for measuring the hydrocarbon content thereof, (iv) pass a second portion of solvent to said receptacle, (v) heat said second portion of solvent to said second temperature, and (vi) pass said heated second portion of solvent to said detecting means for measuring the hydrocarbon content thereof.

* * * * *